(12) United States Patent
Larder et al.

(10) Patent No.: US 6,800,463 B1
(45) Date of Patent: Oct. 5, 2004

(54) METHOD FOR MUTATION DETECTION IN HIV-1 USING POL SEQUENCING

(75) Inventors: Brendan Larder, Churchlane (GB); Sharon Kemp, Churchlane (GB); Stuart Bloor, Biggleswade (GB); Ann Brophy, Cambridge (GB)

(73) Assignee: Virco Bvba, Mechelen (BE)

( * ) Notice: Subject to any disclaimer, the term of this patent is extended or adjusted under 35 U.S.C. 154(b) by 0 days.

(21) Appl. No.: 09/640,787

(22) Filed: Aug. 18, 2000

(30) Foreign Application Priority Data

Apr. 20, 2000 (EP) .......................................... 00201433

(51) Int. Cl.⁷ .............................................. C12P 19/34

(52) U.S. Cl. ........................ 435/91.2; 435/456; 514/44; 536/23.1; 536/23.72; 536/24.3; 536/24.33

(58) Field of Search ................................ 435/91.2, 456; 514/44; 536/23.1, 23.72, 24.3, 24.33

(56) References Cited

U.S. PATENT DOCUMENTS

| | | | |
|---|---|---|---|
| 5,827,648 A | 10/1998 | Eastman et al. ................ | 435/5 |
| 5,837,464 A | 11/1998 | Capon et al. ................... | 435/6 |
| 5,856,086 A | * 1/1999 | Kozal et al. .................... | 435/5 |

FOREIGN PATENT DOCUMENTS

| | | |
|---|---|---|
| EP | 0 617 132 A2 | 9/1994 |
| WO | WO 93/21339 | 10/1993 |
| WO | WO 93/23574 | 11/1993 |
| WO | WO 97/27332 | 7/1997 |
| WO | WO 97/27480 | 7/1997 |
| WO | WO 98/58086 | 12/1998 |
| WO | WO 99/58693 | 11/1999 |
| WO | WO 99/67428 | 12/1999 |

OTHER PUBLICATIONS

Birk et al. Variation in HIV–1 pol gene associated with reduced senetivity to antiretroviral drugs in treatment–naive patients. AIDS (1998) vol. 12 pp. 2369–2375.*
Cabana et al. Emergence and genetic evolution of HIV–1 varients with mutations conferring resistance to multiple reverse transcriptase and protease inhibitors. Journal of Medical Viriology (1999) vol. 59, pp. 480–490.*
Boden et al. HIV–1 drug resistance in newly infected individuals. Journal of the American Medical Association (1999) vol. 282, No. 12, pp. 1135–1141.*
Promega Catalog (2000) pp. 2.7 and 2.11.*
Asseline et al., "Nucleic Acid–Binding Molecules with High Affinity and Base Sequence Specificity: Intercalating Agents Covalently Linked to Oligodeoxynucleotides," *Proc. Natl. Acad. Sci. USA*. vol. 81, pp. 3297–3301 (1984).
Barany, F., "Genetic Disease Detection and DNA Amplification Using Cloned Thermostable Ligase," *Proc. Natl. Acad. Sci. USA*, vol. 88, pp. 189–193 (1991).
Boom et al., "Rapid and Simple Method for Purification of Nucleic Acids," *Journal of Clinical Microbiology*, pp. 495–503 (1990).
Compton, J., "Nucleic Acid Sequence–Based Amplification," *Nature*, vol. 350, pp. 91–92 (1991).
Duck et al., "Probe Amplifier System Based on Chimeric Cycling Oligonucleotides," *BioTechniques*, 9, 142–147 (1990).
Guatelli et al., "Isothermal, In Vitro Amplification of Nucleic Acids by a Multienzyme Reaction Modeled After Retroviral Replication," *Proc. Natl. Acad. Sci. USA*, vol. 87, pp. 1874–1878 (1990).
Kwoh et al., "Transcription–Based Amplification System and Detection of Amplified Human Immunodeficiency Virus Type 1 with a Bead–Based Sandwich Hybridization Format," *Proc. Natl. Acad. Sci. USA*, vol. 86, pp. 1173–1177 (1989).
Landegren et al., "A Ligase–Mediated Gene Detection Technique," *Science*, vol. 241, pp. 1077–1080 (1988).
Lizardi et al., "Exponential Amplification of Recombinant–RNA Hybridization Probes," *Bio/Technology*, vol. 6, pp. 1197–1202 (1988).
Lomell et al., "Quantitative Assays Based on the Use of Replicatable Hybridization Probes," *Clin. Chem.*, 35(9), pp. 1826–1831 (1989).
Matsukura et al., "Phosphorothioate Analogs of Oligodeoxynucleotides: Inhibitors of Replication and Cytopathic Effects of Human Immunodeficiency Virus," *Proc. Natl. Acad. Sci. USA*. vol. 84, pp. 7706–7710 (1987).
Miller et al., "Nonionic Nucleic Acid Analogues. Synthesis and Characterization of Dideoxyribonucleoside Methylphosphonates," *Biochemistry*, vol. 18(23), pp. 5134–5143 (1979).
Nielsen et al., "Sequence–Selective Recognition of DNA by Strand Displacement with a Thymine–Substituted Polyamide," *Science*, vol. 254, pp. 1497–1500 (1991).
Nielsen et al., "Sequence Specific Inhibition of DNA Restriction Enzyme Cleavage by PNA," *Nucleic Acids Research*, vol. 21(2), pp. 197–299 (1993).
Saiki et al., "Genetic Analysis of Amplified DNA with Immobolized Sequence–Specific Oligonucleotide Probes," *Proc. Natl. Acad Sci. USA*. vol. 86, pp. 6230–6234 (1989).

(List continued on next page.)

*Primary Examiner*—Ulrike Winkler
(74) *Attorney, Agent, or Firm*—Woodcock Washburn LLP

(57) ABSTRACT

The present invention relates to a method of for mutation analysis of the HIV pol gene of HIV-1 virions comprising amplifying viral RNA or DNA via nested PCR using outer primers as represented in SEQ ID No: 1 and 2, amplifying said PCR product via nested PCR using a 5' and 3' primer chosen from the inner primers SEQ ID No: 3, 4, 5, and 6, and sequencing this secondary obtained PCR product using at least one sequencing primer chosen from any of SEQ ID No: 7 to 12 or variants thereof. In the alternative, at least one secondary sequencing primer may be used chosen from any of SEQ ID No: 13 to 24. The present invention also relates to kits for performing such a method as well as primers for performing the same.

14 Claims, 1 Drawing Sheet

OTHER PUBLICATIONS

Walker et al., "Isothermal In Vitro Amplification of DNA by a Restriction Enzyme/DNA Polymerase System," *Proc. Natl. Acad. Sci. USA,* vol. 89, pp. 392–396 (1992).

Wu et al., "The Ligation Amplification Reaction (LAR)—Amplification of Specific DNA Sequences Using Sequential Rounds of Template–Dependent Ligation," *Genomics,* 4, pp. 560–569 (1989).

Larder et al., "Quantitative Detection of HIV–1 Drug Resistance Mutations by Automated DNA Sequencing," *Nature,* vol. 365, pp. 671–673 (1993).

Demeter et al., "Interlaboratory Concordance of DNA Sequence Analysis to Detect Reverse Transcriptase Mutations in HIV–1 Proviral DNA," *Journal of Virological Methods,* 75, pp. 93–104 (1998).

Zazzi et al., "Long–Read Direct Infrared Sequencing of Crude PCR Products for Prediction of Resistance to HIV–1 Reverse Transcriptase and Protease Inhibitors," *Molecular Biotechnology,* vol. 10, pp. 1–8, (1998).

Günthard et al., "Comparative Performance of High–Density Oligonucleotide Sequencing and Dideoxynucleotide Sequencing of HIV Type 1 pol from Clinical Samples," *Aids Research and Human Reroviruses,* vol. 14, No. 10, pp. 869–876 (1998).

Puchhammer–Stöck et al., "Comparison of Line Probe Assay (LIPA) and Sequence Analysis for Detection of HIV–1 Drug Resistance," *Journal of Medical Virology,* 57, pp. 283–289 (1999).

Duncan R. Churchill et al., "The Rabbit Study: Ritonavir and Saquinavir in Combination in Saquinavir–Experienced and Previously Untreated Patients," *Aids Research and Human Retroviruses,* Vo. 15 No. 13, pp. 1181–1189 (1999).

Yerly et al., "Transmission of Antiretroviral–drug–resistant HIV–1 Variants," *The Lancet,* vol. 354, pp. 729–733 (1999).

Lorenzi et al., "Impact of Drug Resistance Mutations on Virologic Response to Salvage Therapy," *Aids,* vol. 13, No. 2, pp. F17–F21 (1999).

Schapiro et al., "Clinial Cross Resistance Between the HIV–1 Protease Inhibitors Saquinavir and Indinayir and Correlations with Genotypic Mutations," *Aids,* vol. 13, No. 3, pp. 359–365 (1999).

Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents and Chemotherapy,* pp. 269–276 (1998).

Devereux et al., "Rapid Decline in Detectablility of HIV–1 Drug Resistance Mutations After Stopping Therapy," *Aids,* vol. 13, No. 18, pp. F123–F127 (1999).

Alexander et al., "Prevalence of primary HIV dug resistance among seroconverters during an explosive outbreak of HIV infection among injecting drug users", AIDS, 13, pp. 981–985, (1999).

International Search Report dated Oct. 16, 2001.

P. Kellman and B. A. Larder, "Recombinant Virus Assay: a Rapid, Phenotypic Assay for Assessment of Drug Susceptibility of Human Immunodeficiency Virus Type 1 Isolates", Antimicrobial Agents and Chemotherapy, 38(1), pp. 23–30, (Jan. 1994).

Kojima et al., "Changes in Viremia in Patients Receiving an Alternating or Simultaneous Regimen of AZT and DDI as Assessed by Polymerase Chain Reaction Combined with Reverse Transcription (RNA–PCR)", National Conference of Human Retroviruses and Related Infections, 1, p. 131, (1993).

Larder et al., "Quantitative detection of HIV–1 drug resistance mutations by automated DNA sequencing", Nature, 365, pp. 671–673, (Oct. 14, 1993).

Niubo et al., "Recovery and Analysis of Human Immunodeficiency Virus Type 1 (HIV) RNA Sequences from Plasma Samples with Low HIV RNA Levels", Journal of Clinical Microbiology, 38(1), pp. 309–312, (Jan. 2000).

Sharma et al., "AZT–Related Mutation Lys70Arg in Reverse Transcriptase of Human Immunodeficiency Virus Type 1 Confers Decrease in Susceptibility to ddATP in in Vitro RT Inhibition Assay", Virology, 223, pp. 365–369, (1996).

\* cited by examiner

SEQUENCE LISTING

<160> NUMBER OF SEQ ID NOS: 24

<210> SEQ ID NO 1
<211> LENGTH: 33
<212> TYPE: DNA
<213> ORGANISM: Human immunodeficiency virus type 1

<400> SEQUENCE: 1
cattgctctc caattactgt gatatttctc atg        33

<210> SEQ ID NO 2
<211> LENGTH: 24
<212> TYPE: DNA
<213> ORGANISM: Human immunodeficiency virus type 1

<400> SEQUENCE: 2
gcccctagga aaagggctg ttgg        24

<210> SEQ ID NO 3
<211> LENGTH: 29
<212> TYPE: DNA
<213> ORGANISM: Human immunodeficiency virus type 1

```
<400> SEQUENCE: 3
cctaggaaaa agggctgttg gaaatgtgg                                29

<210> SEQ ID NO 4
<211> LENGTH: 31
<212> TYPE: DNA
<213> ORGANISM: Human immunodeficiency virus type 1

<400> SEQUENCE: 4
ctaactggta ccataatttc actaagggag g                             31

<210> SEQ ID NO 5
<211> LENGTH: 25
<212> TYPE: DNA
<213> ORGANISM: Human immunodeficiency virus type 1

<400> SEQUENCE: 5
catctacata gaaagtttct gctcc                                    25

<210> SEQ ID NO 6
<211> LENGTH: 25
<212> TYPE: DNA
<213> ORGANISM: Human immunodeficiency virus type 1

<400> SEQUENCE: 6
ctaggaaaaa gggctgttgg aaatg                                    25

<210> SEQ ID NO 7
<211> LENGTH: 19
<212> TYPE: DNA
<213> ORGANISM: Human immunodeficiency virus type 1

<400> SEQUENCE: 7
gagagcttca ggtttgggg                                           19

<210> SEQ ID NO 8
<211> LENGTH: 18
<212> TYPE: DNA
<213> ORGANISM: Human immunodeficiency virus type 1

<400> SEQUENCE: 8
aattgggcct gaaaatcc                                            18

<210> SEQ ID NO 9
<211> LENGTH: 20
<212> TYPE: DNA
<213> ORGANISM: Human immunodeficiency virus type 1

<400> SEQUENCE: 9
cctccattcc tttggatggg                                          20

<210> SEQ ID NO 10
<211> LENGTH: 17
<212> TYPE: DNA
<213> ORGANISM: Human immunodeficiency virus type 1

<400> SEQUENCE: 10
ctcccactca ggaatcc                                             17

<210> SEQ ID NO 11
<211> LENGTH: 19
<212> TYPE: DNA
```

-continued

<213> ORGANISM: Human immunodeficiency virus type 1

<400> SEQUENCE: 11
gtactgtcca tttatcagg                                                19

<210> SEQ ID NO 12
<211> LENGTH: 21
<212> TYPE: DNA
<213> ORGANISM: Human immunodeficiency virus type 1

<400> SEQUENCE: 12
cttcccagaa gtcttgagtc c                                             21

<210> SEQ ID NO 13
<211> LENGTH: 21
<212> TYPE: DNA
<213> ORGANISM: Human immunodeficiency virus type 1

<400> SEQUENCE: 13
cagaccagag ccaacagccc c                                             21

<210> SEQ ID NO 14
<211> LENGTH: 19
<212> TYPE: DNA
<213> ORGANISM: Human immunodeficiency virus type 1

<400> SEQUENCE: 14
cactctttgg caacgaccc                                                19

<210> SEQ ID NO 15
<211> LENGTH: 20
<212> TYPE: DNA
<213> ORGANISM: Human immunodeficiency virus type 1

<400> SEQUENCE: 15
ggtacagtat tagtaggacc                                               20

<210> SEQ ID NO 16
<211> LENGTH: 20
<212> TYPE: DNA
<213> ORGANISM: Human immunodeficiency virus type 1

<400> SEQUENCE: 16
gtactggatg tgggtgatgc                                               20

<210> SEQ ID NO 17
<211> LENGTH: 19
<212> TYPE: DNA
<213> ORGANISM: Human immunodeficiency virus type 1

<400> SEQUENCE: 17
gtgggaaaat tgaattggg                                                19

<210> SEQ ID NO 18
<211> LENGTH: 20
<212> TYPE: DNA
<213> ORGANISM: Human immunodeficiency virus type 1

<400> SEQUENCE: 18
gggtcataat acactccatg                                               20

<210> SEQ ID NO 19
<211> LENGTH: 19

```
<212> TYPE: DNA
<213> ORGANISM: Human immunodeficiency virus type 1

<400> SEQUENCE: 19
ggaatattgc tggtgatcc                                          19

<210> SEQ ID NO 20
<211> LENGTH: 20
<212> TYPE: DNA
<213> ORGANISM: Human immunodeficiency virus type 1

<400> SEQUENCE: 20
cattgtttaa cttttgggcc                                         20

<210> SEQ ID NO 21
<211> LENGTH: 18
<212> TYPE: DNA
<213> ORGANISM: Human immunodeficiency virus type 1

<400> SEQUENCE: 21
gataaaacct ccaattcc                                           18

<210> SEQ ID NO 22
<211> LENGTH: 18
<212> TYPE: DNA
<213> ORGANISM: Human immunodeficiency virus type 1

<400> SEQUENCE: 22
gtacagaaat ggaaaagg                                           18

<210> SEQ ID NO 23
<211> LENGTH: 18
<212> TYPE: DNA
<213> ORGANISM: Human immunodeficiency virus type 1

<400> SEQUENCE: 23
ggatgatttg tatgtagg                                           18

<210> SEQ ID NO 24
<211> LENGTH: 20
<212> TYPE: DNA
<213> ORGANISM: Human immunodeficiency virus type 1

<400> SEQUENCE: 24
ggatgtggta ttcctaattg                                         20
```

METHOD FOR MUTATION DETECTION IN HIV-1 USING POL SEQUENCING

CROSS REFERENCE TO RELATED APPLICATIONS

This Application claims priority to European Application No. 00201433.0, filed Apr. 20, 2000, which is incorporated herein by reference in its entirety.

FIELD OF THE INVENTION

The present invention relates to a method for detecting mutations within the HIV pol gene of HIV-1 isolates and in particular with the design of amplification primers and sequencing primers for use in the analysis of the coding domains for the protease and reverse transcriptase, respectively.

BACKGROUND OF THE INVENTION

The availability of rapid, high-throughput automated DNA sequencing technology has obvious applications in clinical research, including the detection of variations in virus populations and mutations responsible for drug resistance in virus genomes. However, analysis of clinical samples by manual sequencing or polymerase chain reaction-(PCR) based point mutation assays has revealed that complex mixtures of wild type and mutant HIV-1 genomes can occur during drug therapy. Therefore, to assess the likely susceptibility of a virus population to a particular drug therapy, it would be desirable to perform DNA sequence analysis that can simultaneously quantitate several resistance mutations in multiple genomes. A particular advantage of analyzing the sequence of more than one pol gene enzyme (Protease and Reverse transcriptase) is that the studied material reflects to a greater extent the viral genetic diversity in the particular patient being investigated.

SUMMARY OF THE INVENTION

The aim of the present invention is thus to provide a reliable sequence analysis method and kit for performing mutation analysis of the pol gene of HIV-1 virus isolates.

In one embodiment, the present invention relates to a method for mutation analysis of the HIV pol gene of a HIV-1 virion comprising the steps of:
a) isolation of a sample comprising HIV-1 RNA,
b) amplifying RNA using outer primers as represented in SEQ ID No: 1 (OUT3) and 2 (PRTO-5),
c) amplifying the product of (b) using a 5' and 3' primer chosen from the inner primers as represented in SEQ ID No: 3 (PCR2.5), 4 (PCR2.3), 5 (SK107) and 6 (SK108), and
d) sequencing this secondary obtained product.

The present invention also provides a method for mutation analysis of the HIV pol gene of HIV-1 isolates comprising the steps of:
a) isolation of a sample comprising HIV-1 DNA,
b) amplifying DNA using outer primers as represented in SEQ ID No: 1 (OUT3) and 2 (PRTO-5),
c) amplifying the product of (b) using a 5' and 3' primer chosen from the inner primers as represented in SEQ ID No: 3 (PCR2.5), 4 (PCR2.3), 5 (SK107) and 6 (SK108), and
d) sequencing this secondary obtained product.

The present invention also relates to a primer as described herein (see Table 1) and used to analyze the sequence of the HIV pol gene of HIV-1 isolates. In a further embodiment, the present invention relates to a diagnostic kit for the mutation analysis of the HIV pol gene of HIV-1 isolates comprising at least one of the primers as shown in Table 1.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

DETAILED DESCRIPTION OF THE INVENTION

Figure 1:
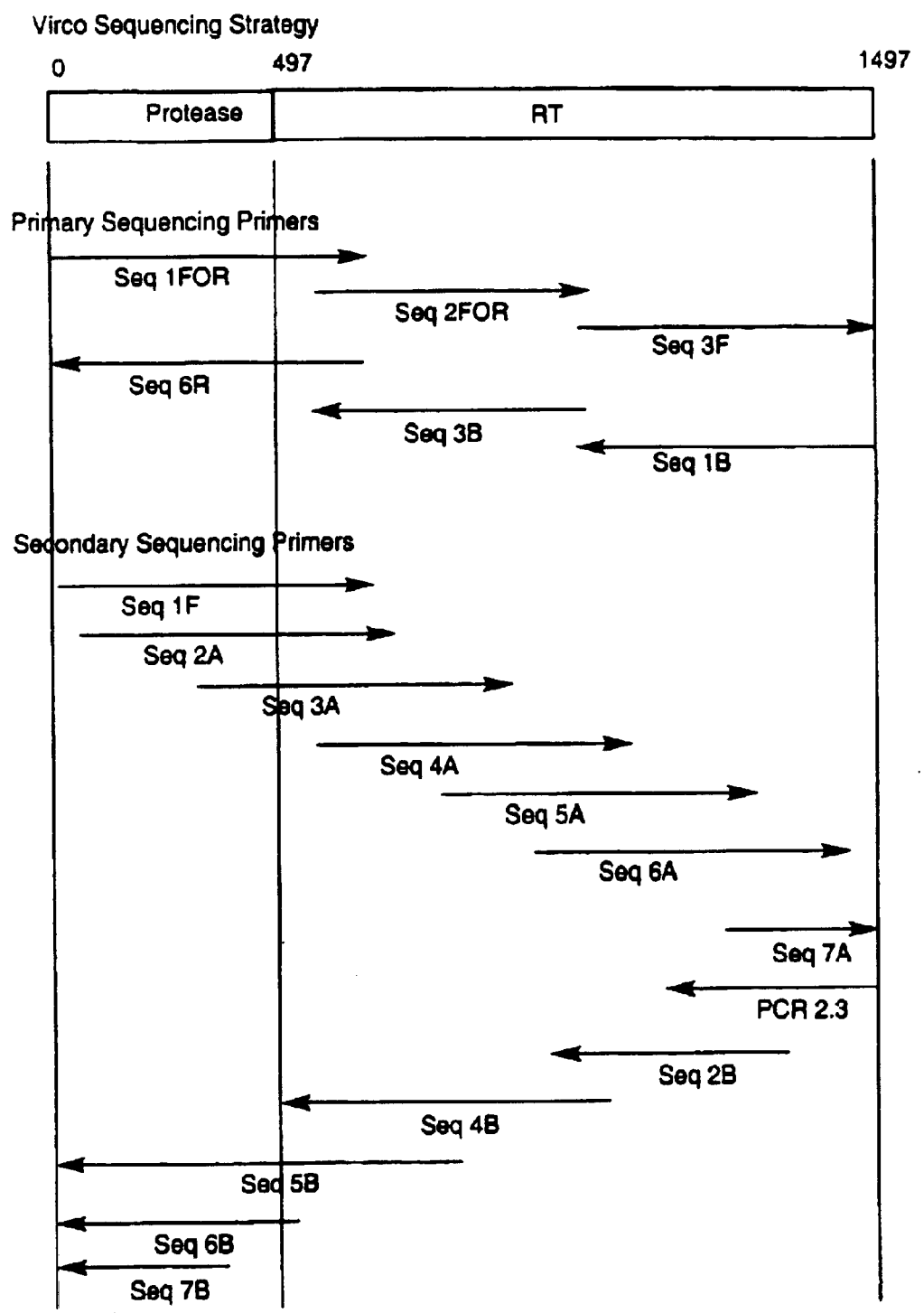
FIG. 1: Schematic overview of the total coding region of the protease-RT coding domain of HIV-1 isolates. The length in nucleotides of both coding regions is indicated. Regions that are sequenced using respectively mentioned sequencing primers are shown. Primary sequences and the secondary sequences are schematically presented.

The present invention, in one aspect, relates to a method for mutation analysis of the HIV pol gene of a HIV-1 virion comprising the steps of:
a) isolation of a sample comprising HIV-1 RNA,
b) PCR amplifying RNA using outer primers as represented in SEQ ID No: 1 (OUT3) and 2 (PRTO-5),
c) PCR amplifying said PCR product using a 5' and 3' primer chosen from the inner primers as represented in SEQ ID No: 3 (PCR2.5), 4 (PCR2.3), 5 (SK107) and 6 (SK108), and
d) sequencing this secondary obtained PCR product.

In a preferred embodiment, the amplifying is via nested PCR. The secondary obtained PCR product may be sequenced using at least one sequencing primer chosen from any of SEQ ID No: 7 to 12 (Seq1FOR, Seq2FOR, Seq3F, Seq1B, Seq3B, Seq6R, Seq1F, Seq2A, Seq3A, Seq5A, Seq7A, Seq2B, Seq4B, Seq6B, Seq7B, Seq4A, Seq6A, Seq5B; see Table 1). In one embodiment, RNA is viron RNA extracted from the sample. In another embodiment, RNA is cell RNA extracted from an infected cell sample.

The present invention describes a mutation analysis of the pol gene of HIV-1 isolates including group M and group O viruses, in particular group M viruses. Mixed populations carrying mutations can be detected when present down to at least 20%.

The present invention also provides a method for mutation analysis of the HIV pol gene of HIV-1 isolates comprising the steps of:
a) isolation of a sample comprising HIV-1 DNA,
b) PCR amplifying DNA using outer primers as represented in SEQ ID No: 1 (OUT3) and 2 (PRTO-5),
c) PCR amplifying said PCR product using a 5' and 3' primer chosen from the inner primers as represented in SEQ ID No: 3 (PCR2.5), 4 (PCR2.3), 5 (SK107) and 6 (SK108), and
d) sequencing this secondary obtained PCR.

In one embodiment, the amplifying is via nested PCR. The secondary obtained PCR product may be sequenced using at least one sequencing primer chosen from any of SEQ ID No: 7 to 12 (Seq1FOR, Seq2FOR, Seq3F, Seq1B, Seq3B, Seq6R, Seq1F, Seq2A, Seq3A, Seq5A, Seq7A, Seq2B, Seq4B, Seq6B, Seq7B, Seq4A, Seq6A, Seq5B; see Table 1). In one embodiment, DNA is viral DNA extracted from the isolated sample material.

According to a preferred method said secondary PCR product is sequenced using a primer as represented in SEQ ID No: 7 (Seq1FOR).

According to a preferred method said secondary PCR product is sequenced using a primer as represented in SEQ ID No: 8 (Seq2FOR).

According to a preferred method said secondary PCR product is sequenced using a primer as represented in SEQ ID No: 9 (Seq3F).

According to a preferred method said secondary PCR product is sequenced using a primer as represented in SEQ ID No: 10 (Seq1B).

According to a preferred method said secondary PCR product is sequenced using a primer as represented in SEQ ID No: 11 (Seq3B).

According to a preferred method said secondary PCR product is sequenced using a primer as represented in SEQ ID No: 12 (Seq6R).

The present invention also provides a method according to the present invention wherein one of the initial sequencing primers is replaced by one or a pair of replacement primers (Table 2). For example, if Seq2FOR (SEQ ID No: 8) failed it is replaced by Seq3A (SEQ ID No: 15) and Seq5A (SEQ ID No: 16). However in principle any described primer that obtains sequence from the region that Seq2FOR (SEQ ID No: 8) was expected to cover can be used i.e. Seq3A (SEQ ID No: 15), Seq4A (SEQ ID No: 22) or Seq5A (SEQ ID No: 16) (see FIG. 1). In addition, Seq6A (SEQ ID No: 23) and Seq5B (SEQ ID No: 24) were also not proposed to replace a specific initial primer but can be used to cover respective sequence domains (see FIG. 1).

In preferred methods according to the present invention the initial sequencing primer as represented in SEQ ID No 7 (Seq 1FOR) is replaced by a primer set as represented in SEQ ID No: 13 (Seq1F) and 14 (Seq2A).

In preferred methods according to the present invention the initial sequencing primer as represented in SEQ ID No 8 (Seq2FOR) is replaced by a primer set as represented in SEQ ID No: 15 (Seq3A) and 16 (Seq5A).

In preferred methods according to the present invention the initial sequencing primer as represented in SEQ ID No 9 (Seq3F) is replaced by a primer set as represented in SEQ ID No: 16 (Seq5A) and 17 (Seq7A).

In preferred methods according to the present invention the initial sequencing primer as represented in SEQ ID No 10 (Seq 1B) is replaced by a primer set as represented in SEQ ID No: 4 (PCR2.3) and 18 (Seq2B).

In preferred methods according to the present invention the initial sequencing primer as represented in SEQ ID No 11 (Seq3B) is replaced by a primer set as represented in SEQ ID No: 18 (Seq2B) and 19 (Seq4B).

In preferred methods according to the present invention the initial sequencing primer as represented in SEQ ID No 12 (Seq6R) is replaced by a primer set as represented in SEQ ID No: 20 (Seq6B) and 21 (Seq7B).

Preferably, the methods according to present invention involve a sequencing step wherein said secondary PCR product is sequenced using a primer as represented in SEQ ID No 13 (Seq1F).

Preferably, the methods according to present invention involve a sequencing step wherein said secondary PCR product is sequenced using a primer as represented in SEQ ID No 14 (Seq2A).

Preferably, the methods according to present invention involve a sequencing step wherein said secondary PCR product is sequenced using a primer as represented in SEQ ID No 15 (Seq3A).

Preferably, the methods according to present invention involve a sequencing step wherein said secondary PCR product is sequenced using a primer as represented in SEQ ID No 16 (Seq5A).

Preferably, the methods according to present invention involve a sequencing step wherein said secondary PCR product is sequenced using a primer as represented in SEQ ID No 17 (Seq7A).

Preferably, the methods according to present invention involve a sequencing step wherein said secondary PCR product is sequenced using a primer as represented in SEQ ID No 18 (Seq2B).

Preferably, the methods according to present invention involve a sequencing step wherein said secondary PCR product is sequenced using a primer as represented in SEQ ID No 19 (Seq4B).

Preferably, the methods according to present invention involve a sequencing step wherein said secondary PCR product is sequenced using a primer as represented in SEQ ID No 20 (Seq6B).

Preferably, the methods according to present invention involve a sequencing step wherein said secondary PCR product is sequenced using a primer as represented in SEQ ID No 21 (Seq7B).

Preferably, the methods according to present invention involve a sequencing step wherein said secondary PCR product is sequenced using a primer as represented in SEQ ID No 22 (Seq4A).

Preferably, the methods according to present invention involve a sequencing step wherein said secondary PCR product is sequenced using a primer as represented in SEQ ID No 23 (Seq6A).

Preferably, the methods according to present invention involve a sequencing step wherein said secondary PCR product is sequenced using a primer as represented in SEQ ID No 24 (Seq5B).

A primer acts as a point of initiation for synthesis of a primer extension product that is complementary to the nucleic acid strand to be copied. The place of hybridization is determined by the primer- and target sequence. As known by the skilled person in the art, specificity of the annealing can be guaranteed by choosing a sequence domain within the target sequence, which is unique, compared to other non-target sequences. Nevertheless, start and stop of the primer onto the target sequence may be located some nucleotides up- or downstream the defined primer site without interfering with this specificity.

Consequently, the present invention also provides a method as described above wherein the sequencing primer is chosen up to 1, 2, 3 or 4 nucleotides upstream or downstream the described primer region.

The present invention also provides a method as described above wherein the outer primer is chosen up to 1, 2, 3 or 4 nucleotides upstream or downstream the described primer region.

The present invention also provides a method as described above wherein the inner primer is chosen up to 1, 2, 3 or 4 nucleotides upstream or downstream the described primer region.

The present invention also provides a method as described above wherein the sample contains free virion particles or virus infected cells.

In particular, the present invention also provides a method as described above wherein the sample is any biological material taken either directly from the infected human being (or animal), or after culturing (enrichment). Biological material may be, e.g., expectorations of any kind, broncheolavages, blood (plasma, serum), skin tissue, biopsies, sperm, semen, lymphocyte blood culture material, colonies, liquid cultures, fecal samples, urine etc.

The present invention also relates to a primer as described above (see Table 1) and used to analyze the sequence of the HIV pol gene of HIV-1 isolates.

Preferentially, such methods according to the present invention involve the sequencing of the defined primary PCR product.

The present invention also relates to a diagnostic kit for the mutation analysis of the HIV pol gene of HIV-1 isolates comprising at least one of the primers as shown in Table 1. The following definitions serve to illustrate the terms and expressions used in the present invention.

The term "drug-induced mutation" means any mutation different from consensus wild-type sequence, more in particular it refers to a mutation in the HIV protease or RT coding region that, alone or in combination with other mutations, confers a reduced susceptibility of the isolate to the respective drug.

The term "target sequence" as referred to in the present invention describes the nucleotide sequence of the wild type, polymorphic or drug induced variant sequence of the protease and RT gene of HIV-1 isolates to be specifically detected by sequence analysis according to the present invention. This nucleotide sequence may encompass one or several nucleotide changes. Target sequences may refer to single nucleotide positions, nucleotides encoding amino acids or to sequence spanning any of the foregoing nucleotide positions. In the present invention said sequence often includes one or two variable nucleotide positions.

It is to be understood that the complement of said target sequence is also a suitable target sequence in some cases.

The target material in the samples to be analyzed may either be DNA or RNA, e.g., genomic DNA, cDNA, messenger RNA, viral RNA or amplified versions thereof. These molecules are also termed polynucleic acids. It is possible to use DNA or RNA molecules from HIV samples in the methods according to the present invention.

Well-known extraction and purification procedures arc available for the isolation of RNA or DNA from a sample, (e.g., in Maniatis et al., Molecular Cloning: A Laboratory Manual, $2^{nd}$ Edition, Cold Spring Harbor Laboratory Press (1989), the disclosure of which is hereby incorporated by reference).

The term "primer" refers to single stranded sequence-specific oligonucleotide capable of acting as a point of initiation for synthesis of a primer extension product that is complementary to the nucleic acid strand to be copied. The length and the sequence of the primer must be such that they allow priming the synthesis of the extension products.

Preferentially, the primer is about 5–50 nucleotides long. Specific length and sequence will depend on the complexity of the required DNA or RNA targets, as well on the conditions of primer use such as temperature and ionic strength.

The fact that amplification primers do not have to match exactly with the corresponding template to warrant proper amplification is ample documented in the literature (Kwok, S., Kellog, D., McKinney, N., Spasic, D., Goda, L., Levenson, C. and Sinisky, J., Effects of primer-template mismatches on the polymerase chain reaction: Human immunodeficiency views type 1 model studies, *Nucl. Acids Res.*, 18, 999 (1990), the disclosure of which is hereby incorporated by reference.).

The amplification method used can be either polymerase chain reaction (PCR; Saiki R, Walsh P, Levenson C, Erlich H., Genetic analysis of amplified DNA with immobilized sequence-specific oligonucleotide probes, *Proc Natl Acad Sci USA*, 86,6230–6234 (1989)), ligase chain reaction (LCR;. Landgren, U; Kaiser, R; Sanders, J; Hood, L., A ligase-mediated gene detection technique, *Science*, 241, 1077–1080 (1988); Wu, D; Wallace, B., The ligation amplification reaction (LAR)- amplification of specific DNA sequences using sequential rounds of template-dependent ligation. *Genomics*, 4, 560–569 (1989); Barany, F., Genetic disease detection and DNA amplification using cloned thermostable ligase. *Proc. Natl. Acad Sci USA*, 88,189–193 (1991)), nucleic acid sequence-based amplification (NASBA; Guatelli, J C; Whitfield, K M; Kwoh, D Y; Barringer, K J, Richman, D D; Gingeras, T R., Isothermal, in vitro amplification of nucleic acids by a multienzyme reaction modeled after retroviral replication. *Proc. Natl. Acad. Sci USA*, 87, 1874–1878 (1990); Compton, J., Nucleic acid sequence-based amplification. *Nature*, 350, 91–92 (1991)), transcription-based amplification system (TAS; Kwoh, D; Davis, G; Whitfield, K; Chappelle, H; Dimichele, L; Gingeras, T., Transcription-based amplification system and detection of amplified human immunodeficiency virus type 1 with a bead-based sandwich hybridization format, *Proc. Natl. Acad Sci USA*, 86,1173–1177 (1989)), strand displacement amplification (SDA; Duck, P., Probe amplifier system based on chimeric cycling oligonucleotides, *Biotechniques*, 9, 142–147 (1990); Walker, G; Little, M; Nadeau, J; Shank, D., Isothermal in vitro amplification of DNA by a restriction enzyme/DNA polymerase system, *Proc. Natl. Acad Sci USA*, 89, 392–396 (1992)) or amplification by means of Qss replicase (Lizardi, P; Guerra, C; Lomeli, H; Tussie-Luna, I; Kramer, F., Exponential amplification of recombinant RNA hybridization probes, *Bio/Technology*, 6,1197–1202 (1988); Lomeli, H; Tyagi, S; Printchard, C; Lisardi, P; Kramer, F., Quantitative assays based on the use of replicatable hybridization probes. *Clin. Chem.*, 35,1826–1831 (1989)) or any other suitable method to amplify nucleic acid molecules known in the art. The disclosures of the above listed references are hereby incorporated by reference.

The oligonucleotides used as primer may also comprise nucleotide analogues such as phosphothiates (Matsukura M, Shinozuka K, Zon G, Mitsuya H, Reitz M, Cohen J, Broder S., Phosphorothioate analogs of oligodeoxynucleotides: inhibitors of replication and cytopathic effects of human immunodeficiency virus, *Proc. Natl. Acad. Sci. USA*, 84, 7706–10 (1987)), alkylphosphorothiates (Miller P, Yano J, Yano E, Carroll C, Jayaram K, Ts'o P., Nonionic nucleic acid analogues. Synthesis and characterization of dideoxyribonucleoside methylphosphonates, *Biochemistry*, 18, 5134–43 (1979)) or peptide nucleic acids (Nielsen P, Egholm M, Berg R, Buchardt O., Sequence-selective of DNA by strand displacement with a thymine-substituted polyamide, *Science*, 254, 1497–500 (1991); Nielsen P, Egholm M, Berg R; Buchardt O., Sequence specific inhibition of DNA restriction enzyme cleavage by PNA, *Nucleic-Acids-Res.*, 21, 197–200 (1993)) or may contain intercalating agents (Asseline U, Delarue M, Lancelot G, Toulme F, Thuong N., Nucleic acidbinding molecules with high affinity and base sequence specificity: intercalating agents covalently linked to oligodeoxynucleotides. *Proc. Natl. Acad. Sci. USA* 81, 3297–301 (1984)). The disclosures of the above listed references are hereby incorporated by reference.

The figures, tables and examples as given below exemplify the present invention. These data are not meant to limit the scope of the present invention.

| NAME | SEQUENCE | SEQ ID N° |
|---|---|---|
| | cDNA synthesis and first round PCR | |
| OUT3 | 5'-CAT-TGC-TCT-CCA-ATT-ACT-GTG-ATA-TTT-CTC-ATG-3' | SEQ ID 1 |
| PRTO-5 | 5'GCC-CCT-AGG-AAA-AAG-GGC-TGT-TGG-3' | SEQ ID 2 |
| | Second round (nested) PCR | |
| Set A | | |
| PCR2.5 | 5'-CCT-AGG-AAA-AAG-GGC-TGT-TGG-AAA-TGT-GG-3' | SEQ ID 3 |
| PCR2.3 | 5'-CTA-ACT-GGT-ACC-ATA-ATT-TCA-CTA-AGG-GAG-G-3' | SEQ ID 4 |
| Set B | | |
| SK107 | 5'-CAT-CTA-CAT-AGA-AAG-TTT-CTG-CTC-C-3' | SEQ ID 5 |
| SK108 | 5'-CTA-GGA-AAA-AGG-GCT-GTT-GGA-AAT-G-3' | SEQ ID 6 |
| | Primary Sequencing primers | |
| Seq1FOR | 5'-GAG-AGC-TTC-AGG-TTT-GGG-G-3' | SEQ ID 7 |
| Seq2FOR | 5'-AAT-TGG-GCC-TGA-AAA-TCC-3' | SEQ ID 8 |
| Seq3F | 5'-CCT-CCA-TTC-CTT-TGG-ATG-GG-3' | SEQ ID 9 |
| Seq1B | 5'-CTC-CCA-CTC-AGG-AAT-CC-3' | SEQ ID 10 |
| Seq3B | 5'-GTA-CTG-TCC-ATT-TAT-CAG-G-3' | SEQ ID 11 |
| Seq6R | 5'-CTT-CCC-AGA-AGT-CTT-GAG-TCC-3' | SEQ ID 12 |
| | Secondary sequencing primers | |
| Seq1F | 5'-CAG-ACC-AGA-GCC-AAC-AGC-CCC-3' | SEQ ID 13 |
| Seq2A | 5'-CAC-TCT-TTG-GCA-ACG-ACC-C-3' | SEQ ID 14 |
| Seq3A | 5'-GGT-ACA-GTA-TTA-GTA-GGA-CC-3' | SEQ ID 15 |
| Seq5A | 5'-GTA-CTG-GAT-GTG-GGT-GAT-GC-3' | SEQ ID 16 |
| Seq7A | 5'-GTG-GGA-AAA-TTG-AAT-TGG-G-3' | SEQ ID 17 |
| PCR2.3 | 5'-CTA-ACT-GGT-ACC-ATA-ATT-TCA-CTA-AGG-GAG-G-3' | SEQ ID 4 |
| Seq2B | 5'-GGG-TCA-TAA-TAC-ACT-CCA-TG-3' | SEQ ID 18 |
| Seq4B | 5'-GGA-ATA-TTG-CTG-GTG-ATC-C-3' | SEQ ID 19 |
| Seq6B | 5'-CAT-TGT-TTA-ACT-TTT-GGG-CC-3' | SEQ ID 20 |
| Seq7B | 5'-GAT-AAA-ACC-TCC-AAT-TCC-3' | SEQ ID 21 |
| Seq4A | 5'-GTA-CAG-AAA-TGG-AAA-AGG-3' | SEQ ID 22 |
| Seq6A | 5'-GGA-TGA-TTT-GTA-TGT-AGG-3' | SEQ ID 23 |
| Seq5B | 5'-GGA-TGT-GGT-ATT-CCT-AAT-TG-3' | SEQ ID 24 |

Table 2: Replacement or secondary sequencing primers. Initial preferred sequencing primers can be replaced by a set of possible replacement primers. Suggestions are indicated in the table.

| Initial sequencing primer | Preferences set of replacement sequencing primers |
|---|---|
| Seq1FOR | Seq1F & Seq2A |
| Seq2FOR | Seq3A & Seq5A |
| Seq3F | Seq5A & Seq7A |
| Seq1B | PCR2.3 & Seq 2B |
| Seq3B | Seq2B & Seq4B |
| Seq6R | Seq6B & Seq7B |

Modes for Carrying Out the Invention

A. Amplification of the HIV-1 Protease-Reverse Transcriptase Coding Domain

RNA was isolated from 100 μl of plasma according to the method described by Boom et al., *J. Clin. Microbiol.* 28 (3) 495–503 (1990), and reverse transcribed with the GeneAmp reverse transcriptase kit (Perkin Elmer) as described by the manufacturer using a HIV-1 specific downstream primer (OUT3, see Table 1). Two subsequent nested PCR were set up using specific outer primers (PRTO-5 and OUT3) and inner primers (PCR2.5 and PCR2.3), respectively (see Table 1). The outer primer reaction was done as described in WO97/27480. The inner amplification was performed in a 96 well plate as follows: 4 μl of the outer amplification product was diluted to a final volume of 50 μl using a 10×amplification mix consisting of 5 μl 10×PCR buffer containing 15 mM $MgCl_2$, 1 μl dNTP's (10 mM) 0.5 μl PCR2.5 (0.25 μg/ml), 0.5 μl PCR2.3 (0.25 μg/ml), 0.4 μl Expand High Fidelity (3.5 U/μl) and MQ water. Amplification was initiated after a short denaturation of the amplification product made using the outer primers (2 min at 94° C.). 10 amplification cycles were started consisting of a 15 sec denaturation step at 94° C., a 30 sec annealing step at 60° C. and a 2 min polymerase step at 72° C., respectively. This amplification was immediately followed by 25 cycles consisting of a 15 sec denaturation step at 94° C., a 30 sec annealing step at 60° C. and a x min polymerase step at 72° C., respectively; where x started at 2 min and 5 sec and increased each cycle with 5 sec. Amplification was finalized by an additional polymerase step (7 min at 72° C.). Subsequently, the reaction was held at 4° C. till further analyzed or stored at −20° C. (for short periods) or −70° C. (for longer periods). In order to analyze the amplification products, a DNA agarose gel was run and amplification products were visualized using UV-detection. Obtained PCR products were purified using the QIAquick 96-well plate system as described by the manufacturer (Qiagen).

B. Sequencing of pol Coding Region

The coding domain of the pol gene present on the amplified fragments was analyzed via sequencing using standard sequencing techniques. Preferentially, one started initial with a set of 6 primers (Seq1FOR, Seq2FOR, Seq3F, Seq1B, Seq3B and Seq6R) covering the coding domain of the HIV-protease and reverse transcriptase protein. Sequences and location onto the coding region are shown in Table 1 and FIG. 1, respectively. The sequencing was started by first distributing 4 µl of the primer stocks (4.0 µM) over a 96 well plate where each stock is pipetted down the column. In a second step, master mixes were made consisting of 14 µl MQ, 17.5 µl dilution buffer, 7µl sample (PCR fragment) and 14 µl Big Dye Terminator Mix. A fraction (7.5 µl) of each master mix, containing a specific PCR fragment, was transferred to a specific place into the 96 well plate so that each sample fraction was mixed with a different PCR primer set. Samples were pipetted across the rows. Samples were placed in a thermal cycler and sequencing cycles started. The sequencing reaction consisted of 25 repetitive cycles of 10 sec at 96° C., 5 sec at 50° C. and 4 min at 60° C., respectively. Finally, sequence reactions were held at 4° C. till further analysis or stored as previously described. The sequencing reactions were precipitated using a standard ethanol precipitation procedure, resuspended in 2 µl formamide and heated for 2 minutes at 92° C. in the thermal cycler. Samples were cooled on ice until ready to load. 1 µl of each reaction was loaded on a 4.25% vertical acrylamide gel in a 377 sequencer system and gel was run until separation of the fragments was complete.

C. Sequence Analysis of pol Coding Region

Sample sequences were imported as a specific project into the sequence manager of Sequencher (Genecodes) and compared to the wild type HXB2 Pro/RT reference sequence. Sequences were assembled automatically and set at 85% minimum match. Secondary peaks were searched and the minimum was set at 60%. Any sequence that hung over the 5' end or the 3' end of the reference was deleted. When a region of overlap between sequences from the same strand was reached, the poorest quality of sequence was deleted leaving an overlap of 5–10 bases. Ambiguous base calls are considered poor matches to exact base calls. The sequence assembly was saved within a contig that can be edited.

Obtained sequences were edited so that base calls could be interpreted easily. Ambiguous sequences were retrieved and checked for possible errors or points of heterogeneity. When the point of ambiguity appeared correct (both strands of sequence agree but is different from the reference sequence) it was interpreted to be a variant. The reference sequence was used as an aid for building a contig and a guide to overall size and for trimming, but was not used for deciding base calls. A change was only made when both strands agreed. All gaps were deleted or filled, unless they occur in contiguous groups of a multiple of 3 (I.E. insertion or deletion of complete codons) based on data form both sequence strands. Once the editing was complete, the new contig sequence was saved as a consensus sequence and used for further analysis.

Detailed sequence editing was performed following certain rules: A) ABI primer blobs are trimmed at 5' ends where 1 consecutive base remain off the scale; sequence is trimmed not more than 25% until the first 25 bases contain less than 1 ambiguity; at least first 10 bases from the 5' end are removed, B) 3' ends are trimmed starting 300 bases after the 5' trim; the first 25 bases containing more than 2 ambiguities are removed; trim from 3' end until the last 25 bases contain less than 1 ambiguity. The maximum length of the obtained sequence fragment after trimming is 550 bases.

Sequences that failed to align were removed from the assembly and replaced by data retrieved from new sequence analyses. When further failures occurred, PCR reactions were repeated. Chromatograms were visualized using the IBM software system.

D. Detection of Clonal Clinical Samples-analysis of Limit of Detection for Heterozygous Base Calls A clonal clinical sample was mixed with wild type HXB2 at known ratio's to determine limits of detection of the system. The limit of detection was found to be around 1000 RNA copies/ml from plasma; mixed populations of mutations could be detected when present down to 20%.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method for detection of mutations in the pol gene of HIV-1 isolates comprising the steps of:
   a) isolation of a sample comprising HIV-1 RNA,
   b) PCR amplifying RNA from said sample using an outer primer with SEQ ID No: 1 and SEQ ID No: 2 to obtain a primary PCR product,
   c) PCR amplifying said primary PCR products using a 5' and 3' primer chosen from an inner primer from the group SEQ ID No: 3, SEQ ID No: 4, SEQ ID NO: 5, and SEQ ID No: 6, to obtain a secondary PCR product, and
   d) sequencing said secondary PCR product.

2. A method according to claim 1, wherein said secondary PCR product is sequenced using at least one sequencing primer chosen from SEQ ID No: 7, SEQ ID No: 8, SEQ ED No 9, SEQ ID No: 10, SEQ ID No: 11, and SEQ ID No: 12.

3. A method according to claim 1, wherein said RNA is viron RNA extracted from said sample.

4. A method according to claim 1, wherein said secondary PCR product is sequenced using at least one sequencing primer chosen from SEQ ID NO: 7, SEQ ID No: 8, SEQ ID No: 9, SEQ ID No: 10, SEQ ID No: 11, and SEQ ID No: 12; and wherein at least one of said sequencing primer is replaced by one or a pair of replacement primers, wherein at least one of said replacement primers is at least one from the group SEQ ID No: 13 and SEQ 14 for sequencing primer SEQ ID No: 7, SEQ ID No: 15 and SEQ ID No: 16 for sequencing primer SEQ No: 8, SEQ ID No; 16 and SEQ ID No: 17 for sequencing primer SEQ ID NO: 9, SEQ ID No: 4 and SEQ ID No: 18 for sequencing primer SEQ ID NO: 10, SEQ ID No: 18 and SEQ ID No: 19 for sequencing primer SEQ ID NO: 11, and SEQ ID No: 20 and SEQ ID No: 21 for sequencing primer SEQ ID NO: 12.

5. A method according to claim 1, wherein said secondary PCR product is sequenced using at least one sequencing primer chosen from primers up to 1, 2, 3, or 4 nucleotides upstream or downstream primer regions chosen from at least one of SEQ ID No: 7, SEQ ID No: 8, SEQ ID No: 9, SEQ ID No: 10, SEQ D No: 11, and SEQ ID No: 12.

6. A method according to claim 1, wherein the outer primer is chosen from primers up to 1, 2, 3, or 4 nucleotides upstream or downstream prier region with SEQ ID No: 1 and SEQ ID No: 2.

7. A method according to claim 1, wherein the inner primer is chosen from primers up to 1, 2, 3, or 4 nucleotides upstream or downstream primer region with SEQ ID No: 3, SEQ ID No: 4, SEQ ID No: 5, and SEQ ID No: 6.

8. A method according to claim 1, wherein the sample contains free viron particles or virus infected cells.

9. A method according to claim 1, wherein said primary PCR product is sequenced using at least one sequencing primer chosen from the group SEQ ID No: 7, SEQ ID No: 8, SEQ ID No: 9, SEQ ID No: 10, SEQ ID No: 11, and SEQ ID No: 12.

10. A method according to claim 1, wherein said inner primer has SEQ ID No: 3, SEQ ID No: 4, SEQ ID NO: 5, and SEQ ID No: 6.

11. A method according to claim 10, wherein said outer primer is chosen from primers up to 1, 2, 3, or 4 nucleotides upstream or downstream primer region with SEQ ID No: 1 and SEQ ID No: 2.

12. A method according to claim 10, wherein said inner primer is chosen from primers up to 1, 2, 3, or 4 nucleotides upstream or downstream primer region with SEQ ID No: 3, SEQ ID No: 4, SEQ ID No: 5, and SEQ ID No: 6.

13. A method according to claim 10, wherein said RNA is viron RNA extracted from said sample.

14. A method according to claim 10, wherein said sample contains free viron particles or virus infected cells.

* * * * *

UNITED STATES PATENT AND TRADEMARK OFFICE
CERTIFICATE OF CORRECTION

PATENT NO. : 6,800,463 B1
DATED : October 5, 2004
INVENTOR(S) : Brendan Larder et al.

It is certified that error appears in the above-identified patent and that said Letters Patent is hereby corrected as shown below:

Title page,
Item [56], References Cited, OTHER PUBLICATIONS, "Lomell et al." reference, please delete "Lomell et al.," and insert -- Lomeli et al., -- therefor, and please insert missing reference -- Kwok et al., "Effects of Primer-template Mismatches on the Polymerase Chain Reaction: Human Immunodeficiency Views Type 1 Model Studies." Nucl. Acids Res., 18, 999 (1990). -- therefor.

Column 7,
Line 1, please insert -- Table 1: Sequence of the amplification- and sequencing primers used. Name and sequence identification numbers are indicated. -- therefor.

Signed and Sealed this

Seventeenth Day of May, 2005

JON W. DUDAS
*Director of the United States Patent and Trademark Office*